US006060498A

United States Patent [19]
Ashizawa et al.

[11] Patent Number: 6,060,498
[45] Date of Patent: May 9, 2000

[54] COMPOSITION CONTAINING ANTITUMOR AGENT

[75] Inventors: Kazuhide Ashizawa, Ibaraki; Hidenobu Ando, Gifu, both of Japan

[73] Assignee: Eisai Co., Ltd., Tokyo, Japan

[21] Appl. No.: 09/125,813

[22] PCT Filed: Feb. 26, 1997

[86] PCT No.: PCT/JP97/00560

§ 371 Date: Aug. 26, 1998

§ 102(e) Date: Aug. 26, 1998

[87] PCT Pub. No.: WO97/30706

PCT Pub. Date: Aug. 28, 1997

[30] Foreign Application Priority Data

Feb. 26, 1996 [JP] Japan .................................. 8-037765

[51] Int. Cl.⁷ .................................................. A01N 43/38
[52] U.S. Cl. ........................... 514/415; 548/490; 548/491
[58] Field of Search ............................ 514/415; 548/491, 548/490

[56] References Cited

U.S. PATENT DOCUMENTS 4,416,874 11/1983 Kaplan et al. ........................... 424/177

FOREIGN PATENT DOCUMENTS

| 46-2949 | 10/1971 | Japan . |
| 58-69809 | 4/1983 | Japan . |
| 60-61519 | 4/1985 | Japan . |
| 4-253976 | 9/1992 | Japan . |
| 5-112528 | 5/1993 | Japan . |
| 7-165708 | 6/1995 | Japan . |
| 7165708 | 6/1995 | Japan . |
| 8-231505 | 9/1996 | Japan . |

OTHER PUBLICATIONS

Abstract to Yoshino et al. of J07165708, Jun. 1995.

*Primary Examiner*—Dwayne C. Jones
*Attorney, Agent, or Firm*—Birch, Stewart, Kolasch & Birch, LLP

[57] ABSTRACT

The present invention provides a preparation for injection comprising an antitumor agent which is sparingly soluble in water.

Specifically, it provides a composition containing N-(3-chloro-1H-indol-7-yl)-4-sulfamoylbenzenesulfonamide, which contains N-(3-chloro-1H-indol-7-yl)-4-sulfamoyl-benzenesulfonamide and a basic substance and will provide an aqueous solution having a pH of 7 or higher when dissolved in water.

13 Claims, No Drawings

COMPOSITION CONTAINING ANTITUMOR AGENT

This application is the national phase under 35 U.S.C. §371 of prior PCT International Application Ser. No. PCT/JP97/00560 which has an International filing date of Feb. 26, 1997 which designated the United States of America, the entire contents of which are hereby incorporated by reference.

FIELD OF THE INVENTION

The present invention relates to a composition containing N-(3-chloro-1H-indol-7-yl)-4-sulfamoylbenzenesulfonamide which is an antitumor agent.

PRIOR ART

N-(3-chloro-1H-indol-7-yl)-4-sulfamoylbenzenesulfonamide is an antitumor agent, which terminates multiplication of tumor cells by a novel mechanism of action. The excellent effects of the antitumor agent has been demonstrated by experiments on animals. A group of the compounds encompassing the compound of the present invention is disclosed in JP-A-7-165708. On the other hand, various methods for administering an antitumor agent are known, among which oral administration is generally regarded as the easiest to dose and the least troublesome for a patient. However, oral administration cannot always be applied depending on degrees of progression of the disease of a patient or sites of formation of tumors, so that it often becomes inevitable to form an antitumor agent into a preparation for injection.

N-(3-chloro-1H-indol-7-yl)-4-sulfamoylbenzenesulfonamide is a compound which is sparingly soluble in water. The compound is substantially insoluble in water at a pH around the range of 5 to 7, at which a preparation for injection is commonly used. In general, it is necessary to dissolve a pharmaceutical substance in water for forming a preparation for injection. Therefore, it is very difficult to form the compound of the present invention into a preparation for injection. The inventors of the present invention have intensively studied to obtain an aqueous solution of N-(3-chloro-1H-indol-7-yl)-4-sulfamoylbenzenesulfonamide. As a result of the studies, they have found that an aqueous solution which is safe and stable for a long period and also a preparation for injection thereof can be obtained by the means as described below. The present invention has been accomplished on the basis of this finding.

DISCLOSURE OF THE INVENTION

The present invention relates to a composition containing N-(3-chloro-1H-indol-7-yl)-4-sulfamoylbenzenesulfonamide, which is characterized in that the composition contains N-(3-chloro-1H-indol-7-yl)-4-sulfamoylbenzenesulfonamide and a basic substance and will provide an aqueous solution having a pH of 7 or higher when dissolved in water.

In other words, the present invention provides a pharmaceutical composition containing N-(3-chloro-1H-indol-7-yl)-4-sulfamoylbenzenesulfonamide in a pharmacologically effective dose and a basic substance and providing an aqueous solution having a pH of 7 or higher when dissolved in water.

The basic substance is preferably at least one selected from the group consisting of meglumine, sodium carbonate, monoethanolamine and sodium hydroxide.

Furthermore, the present invention also provides a use of N-(3-chloro-1H-indol-7-yl)-4-sulfamoylbenzenesulfonamide and a basic substance for producing an injection of an antitumor agent.

DETAILED DESCRIPTION OF THE INVENTION

N-(3-chloro-1H-indol-7-yl)-4-sulfamoylbenzenesulfonamide is a novel sulfonamide derivative having a bicyclic heterocycle, which is a compound exhibiting an excellent antitumor activity based on the mechanism of action and having a low toxicity. The compound (hereinafter sometimes referred to as the present compound) is represented by the following structural formula.

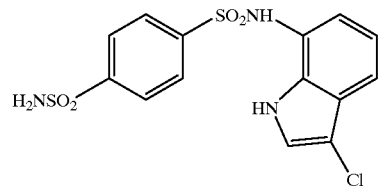

The synthesis of the present compound can be carried out according to the process disclosed in JP-A-7-165708. For example, the present compound can be synthesized as follows. After dissolving 264 mg (2 mmol) of 7-amino-1H-indole in pyridine, 767 mg (3 mmol) of 4-sulfamoylbenzenesulfonyl chloride is added thereto under stirring at room temperature. After the mixture is stirred overnight at room temperature, the solvent is evaporated under reduced pressure. Ethyl acetate and 0.2 N hydrochloric acid are added to the resulting residue. The organic layer is separated, washed with water, and dried over magnesium sulfate, followed by evaporation of the solvent. The resulting residue is purified by silica gel column chromatography to give 445 mg of N-(1H-indol-7-yl)-4-sulfamoylbenzenesulfonamide.

The product thus obtained is dissolved in a mixed solvent of dichloromethane and dimethylformamide, followed by addition of N-chlorosuccinimide under stirring under nitrogen atmosphere. After 1.5 hours of stirring at room temperature, water is added thereto, and the mixture is concentrated. After adding ethyl acetate and 0.2 N hydrochloric acid to the concentrated solution, the organic layer is separated and washed successively with a saturated aqueous solution of sodium bicarbonate and brine. Then the organic layer is dried over magnesium sulfate, followed by evaporating the solvent under reduced pressure. The resulting residue is purified by silica gel column chromatography to give 349 mg of N-(3-chloro-1H-indol-7-yl)-4-sulfamoylbenzenesulfonamide.

In the present invention, a basic substance means a substance of which an aqueous solution is basic when the substance is dissolved in water, and also which can be employed for use in pharmaceuticals. Examples thereof include meglumine, sodium carbonate, monoethanolamine and sodium hydroxide, etc. among which meglumine and sodium carbonate are still preferable. These basic substances may be used singly or as a combination of two or more thereof. The mixing ratio of the basic substance to the present compound is not particularly limited so long as the solution in which the components are dissolved has a pH of 7 or higher. However, the mixing ratio generally is 0.1 to 50 parts by weight of the basic compound to 1 part of the present compound, and more preferably 0.5 to 20 parts by weight. A solution obtained by the composition containing N-(3-chloro-1H-indol-7-yl)-4-sulfamoylbenzenesulfonamide according to the present invention in water or water/a water-soluble organic solvent has a pH of 7 or higher, preferably 8 or higher, more preferably 9 or higher, and still more preferably 10 or higher.

The composition according to the present invention may be formed into various dosage forms for administration, and exerts its excellent effect particularly in a dosage form for injection. Examples of the dosage form include a solution for injection and a freeze-dried preparation. For these dosage forms, conventional substances such as glucose, mannitol, lactose, sodium chloride or the like may be used, and substances such as hydrochloric acid, phosphoric acid or the like may be used for pH adjustment.

According to the present invention, the solubility of the present compound which is extremely difficult to be dissolved in water increases, so that the present compound can be formed into a preparation for injection. This is an object of the present invention.

The production of the composition according to the present invention is not particularly limited. For example, a solution for injection can be prepared as follows. The present compound and a basic substance are each weighed out in a prescribed amount, respectively, followed by addition of distilled water for injection to dissolve the components therein. After filtration, the solution is placed and sealed in an ampule or the like, followed by sterilization. An ampule for injection can be obtained in this manner. Alternatively, a freeze-dried preparation can be prepared, for example, as follows. The present compound and a basic substance are each weighed out in a prescribed amount, respectively, followed by addition of distilled water for injection. A preparation can be obtained in this manner.

The present invention is explained below in more detail by reference to the following examples, but the present invention should not be construed as being limited thereto.

N-(3-chloro-1H-indol-7-yl)-4-sulfamoylbenzenesulfonamide for use in the present invention is also called as N-(3-chloro-7-indolyl)-1,4-benzenedisulfonamide according to the IUPAC nomenclature.

EXAMPLES

Example 1

With 0.1 g of N-(3-chloro-1H-indol-7-yl)-4-sulfamoylbenzenesulfonamide (the present compound), 1.0 g of meglumine was mixed, followed by addition of 5 ml of distilled water for injection thereto and stirring to give a transparent solution.

The solution had a pH of 11.4. This solution was stable even after sterilization for 60 minutes at 115° C.

Example 2

Separate portions of 0.1 g of the present compound were weighed out. Sodium carbonate, monoethanolamine, and sodium hydroxide is separately added to each portion in an amount of 1.0 g, respectively, followed by addition of 5 ml of distilled water for injection thereto and stirring to give transparent solutions.

The respective solutions had a pH of 11.4, 11.8, and 12.3, respectively.

Example 3

Separate portions of 0.1 g of the present compound were weighed out. Then, 0.7 g of meglumine, 1.0 g of sodium carbonate, 1.0 g of monoethanolamine, and 0.7 g of sodium hydroxide is separately added to each portion, followed by addition of 5 ml of distilled water for injection thereto and stirring to give transparent solutions. These respective solutions were subjected to sterilizing filtration and placed in a 10-ml glass vial, respectively, and freeze-dried to obtain solid mixtures.

We claim:

1. A pharmaceutical composition which comprises N-(3-chloro-1H-indol-7-yl)-4-sulfamoylbenzenesulfonamide in a pharmacologically effective dose and a basic substance and will provide an aqueous solution having a pH of 7 or higher when dissolved in water.

2. The composition as claimed in claim 1, wherein the basic substance is at least one selected from the group consisting of meglumine, sodium carbonate, monoethanolamine and sodium hydroxide.

3. The composition as claimed in claim 1, wherein N-(3-chloro-1H-indol-7-yl)-4-sulfamoylbenzenesulfonamide and a basic substance is contained in an amount of 1 part by weight and 0.1 to 50 parts by weight, respectively.

4. The composition as claimed in claim 1, which further comprises water and is an injection.

5. The composition as claimed in claim 1, wherein the basic substance is pharmacologically acceptable.

6. The composition as claimed in claim 1, which is an antitumor agent.

7. The composition as claimed in claim 4, which has a pH of 10 or higher.

8. A method for producing an antitumor agent, comprising the steps of:

(a) dissolving N-(3-chloro-1H-indol-7-yl)-4-sulfamoylbenzenesulfonamide and a basic substance in water, and (b) adjusting the solution to have a pH of not less than 7.

9. The method of claim 8, wherein said basic substance is meglumine.

10. The method of claim 8, wherein said basic substance is sodium hydroxide.

11. The method of claim 9, wherein the mixing ratio of the meglumine to the N-(3-chloro-1H-indol-7-yl)-4-sulfamoylbenzenesulfonamide compound is 0.5 to 20 parts by weight.

12. The method of claim 9, wherein the pH is 9 to 10.

13. The method of claim 9, wherein the pH is greater than 10.

* * * * *